United States Patent
He et al.

(10) Patent No.: US 6,859,520 B2
(45) Date of Patent: Feb. 22, 2005

(54) TRANSMISSION MODE X-RAY DIFFRACTION SCREENING SYSTEM

(75) Inventors: Bob Baoping He, Madison, WI (US); Ryan C. Bollig, Marshall, WI (US); Hans Mathias Lutz Brügemann, Durmersheim (DE)

(73) Assignee: Bruker AXS, Inc., Madison, WI (US)

( * ) Notice: Subject to any disclaimer, the term of this patent is extended or adjusted under 35 U.S.C. 154(b) by 137 days.

(21) Appl. No.: 10/393,441

(22) Filed: Mar. 20, 2003

(65) Prior Publication Data

US 2003/0219099 A1 Nov. 27, 2003

Related U.S. Application Data

(60) Provisional application No. 60/366,417, filed on Mar. 21, 2002.

(51) Int. Cl.[7] .............................................. G01N 23/20
(52) U.S. Cl. .............................. 378/79; 378/81; 378/71
(58) Field of Search ............................ 378/79, 70, 71, 378/81, 208

(56) References Cited

U.S. PATENT DOCUMENTS

| | | | | |
|---|---|---|---|---|
| 5,359,640 A | * | 10/1994 | Fink et al. ..................... | 378/79 |
| 6,005,914 A | * | 12/1999 | Quinn et al. .................. | 378/81 |
| 6,069,934 A | * | 5/2000 | Verman et al. ............... | 378/73 |
| 6,111,930 A | | 8/2000 | Schipper | |
| 6,163,592 A | * | 12/2000 | He et al. ...................... | 378/71 |
| 6,301,330 B1 | * | 10/2001 | Kurtz et al. .................. | 378/71 |
| 6,371,640 B1 | * | 4/2002 | Hajduk et al. .............. | 378/208 |
| 6,457,862 B1 | * | 10/2002 | Sumii et al. ................ | 378/208 |
| 6,507,636 B1 | | 1/2003 | Lehmann | |
| 2001/0036640 A1 | | 11/2001 | D'Amico | |

FOREIGN PATENT DOCUMENTS

WO    WO 00/36405 A2    6/2000

* cited by examiner

*Primary Examiner*—Edward J. Glick
*Assistant Examiner*—Irakli Kiknadze
(74) *Attorney, Agent, or Firm*—Kudirka & Jobse, LLP

(57) ABSTRACT

A transmission mode x-ray diffraction screening system has a sample support that holds a sample tray with multiple samples to be tested. The sample support is connected to a translation stage that is movable in three dimensions, and that it offset from the location of the sample support. An x-ray source is located to one side of the sample support, and a detector is located to the other side, thereby allowing the detection of x-rays that are diffracted by the sample in a transmission mode. A retractable beamstop may be located between the sample and the detector to block at least part of the non-diffracted x-rays from the source. A video camera may also be provided for imaging the sample location, which may be illuminated by a laser. The entire system may be automated such that each sample in the sample tray may be sequentially analyzed.

36 Claims, 4 Drawing Sheets

TRANSMISSION MODE X-RAY DIFFRACTION SCREENING SYSTEM

CROSS-REFERENCE TO RELATED APPLICATIONS

This application takes priority from U.S. Provisional Patent Application No. 60/366,417 filed Mar. 21, 2002.

FIELD OF THE INVENTION

This invention relates generally to the field of x-ray diffraction analysis and, more specifically, to a system for x-ray diffraction screening in combinatorial chemistry.

BACKGROUND OF THE INVENTION

Combinatorial chemistry refers to techniques to fabricate, test, and store the resulting data for a material library containing tens, hundreds or even thousands different materials or compounds. Combinatorial investigations require rapid screening techniques to test and evaluate variations of composition, structure and property within a material library. X-ray diffraction is one of the most suitable screening techniques because abundant information can be revealed from the diffraction pattern and X-ray diffraction is fast and non-destructive.

An x-ray diffraction system for use in combinatorial chemistry was reported on in a recent journal (Bob. B. He, John Anzelmo, Peter LaPuma, Uwe Preckwinkel and Kingsley. L. Smith, "XRD Rapid Screening System for Combinatorial Chemistry", Advances in X-ray Analysis, Vol. 44, the 49th Annual Denver X-ray Conference, Denver, Colo., USA, 2000). All of the components of the system are mounted on a vertical goniometer, and the samples are located a multiple-cell sample tray mounted on a sample support that is movable in three dimensions. An x-ray source and an x-ray detector are each located at an angle relative to the top surface of the sample tray such that x-ray energy from a sample under test is diffracted toward the detector. A laser video system is used for automatic alignment of the sample under test, and allows each sample cell to be sequentially and automatically placed at the testing location.

Although the aforementioned system provides a means for combinatorial screening using automated x-ray diffraction analysis, it is limited to "reflection mode" analysis. That is, the x-ray source and the detector are located to the same side of the sample holder. In certain circumstances, however, it is desirable to perform a sample analysis using "transmission mode" analysis due to various reasons, including the need for low angle diffraction, and advantages when testing thin samples or samples in liquid environments.

SUMMARY OF THE INVENTION

In accordance with the present invention, a transmission mode x-ray diffraction analysis system is provided that performs testing on a plurality of samples in a multiple-cell sample tray. The sample tray is mounted on a sample support that is connected to an offset translation stage. The translation stage is offset away from the region through which x-rays are transmitted from an x-ray source to a sample under test. From the translation stage, which is movable in three dimensions and is preferably motorized, the sample support extends toward the instrument center, which is the position at which the sample under test is located during testing. The sample support supports the sample tray along its outer surface, and does not obstruct the bottom of sample tray below the locations of the sample wells. In this way, an x-ray source on one side of the sample tray can transmit energy to the sample, and x-ray energy can be diffracted toward the sample, without either having to pass through the sample support. The support may also be adjustable so as to accommodate sample trays of different sizes and shapes.

The system may be mounted on a base, and a goniometer can be used to support different components. The use of a goniometer with different relative components attached to different parts of the goniometer allows for relative angles between those components to be changed. For example, a detector, such as a two-dimensional x-ray detector, may be attached to one circle of the goniometer, while, allowing it to be positioned relative to an x-ray source apparatus. This relative angular positioning of these components enables the measurement of different diffraction angles. Also mounted to the goniometer may be a beamstop that, when extended, blocks original x-ray energy from the x-ray source from reaching the detector. The beamstop is preferably retractable so that it may be drawn away from the vicinity of the sample tray to prevent obstruction during changing of the tray or observation of the samples.

Observation and positioning of the samples may be done with a positioning system such as a video camera, possibly with a zoom feature, that focuses on the instrument center. This video system collects data that is used for aligning the sample under test prior to performing the x-ray analysis, and may be used in conjunction with a laser focused on the instrument center. The positioning system works in conjunction with the translation stage to adjust the positions of the samples to enable the automatic sequential testing of each of the samples in the sample tray. Preferably, the positioning system is connected to a movable part of the goniometer, allowing it to be moved following a sample positioning operation. After diffraction analysis of a sample under test, the motor in the translation stage is operated to move a new sample cell to the instrument center. The video positioning system is moved to the correct location for observation, allowing the sample to be precisely positioned, after which the beamstop may be extended and the new diffraction analysis may be performed. Once the relevant data is collected, the beamstop is retracted, and the translation stage is once again operated to move the next sample cell into position. This process continues until each sample is tested. A software routine may be used to control the automated sample process.

The system may also be used in either a "beam-up" or a "beam-down" configuration. In the beam-up configuration, the x-ray source is located below the sample tray, such that the x-ray energy passes through a bottom surface of the sample tray prior to encountering the sample. In the beam-down configuration, the x-ray energy encounters the sample after which the diffracted x-ray energy passes through the bottom surface of the sample tray prior to reaching the detector. The mounting of system components to a goniometer simplifies the adjustment of the system between the beam-up and beam-down configurations. Different sample trays may also be provided to take advantage of the specific configuration. One sample tray has shallow sample wells with empty spaces underneath each through which x-ray energy from the x-ray source would pass in a beam-up configuration, prior to reaching the bottom surface of the sample well containing the sample under test. In a sample tray more appropriate for use in a beam-down configuration, the sample wells are deep, each having a significant empty space above the surface of the sample contained therein. In yet another sample tray configuration, the overall profile of the tray is thin, with shallow sample wells having thin bottom surfaces. Such a sample tray may be used in either the beam-up or the beam-down configuration.

BRIEF DESCRIPTION OF THE DRAWINGS

The above and further advantages of the invention may be better understood by referring to the following description in conjunction with the accompanying drawings in which.

DETAILED DESCRIPTION

Figure 1:
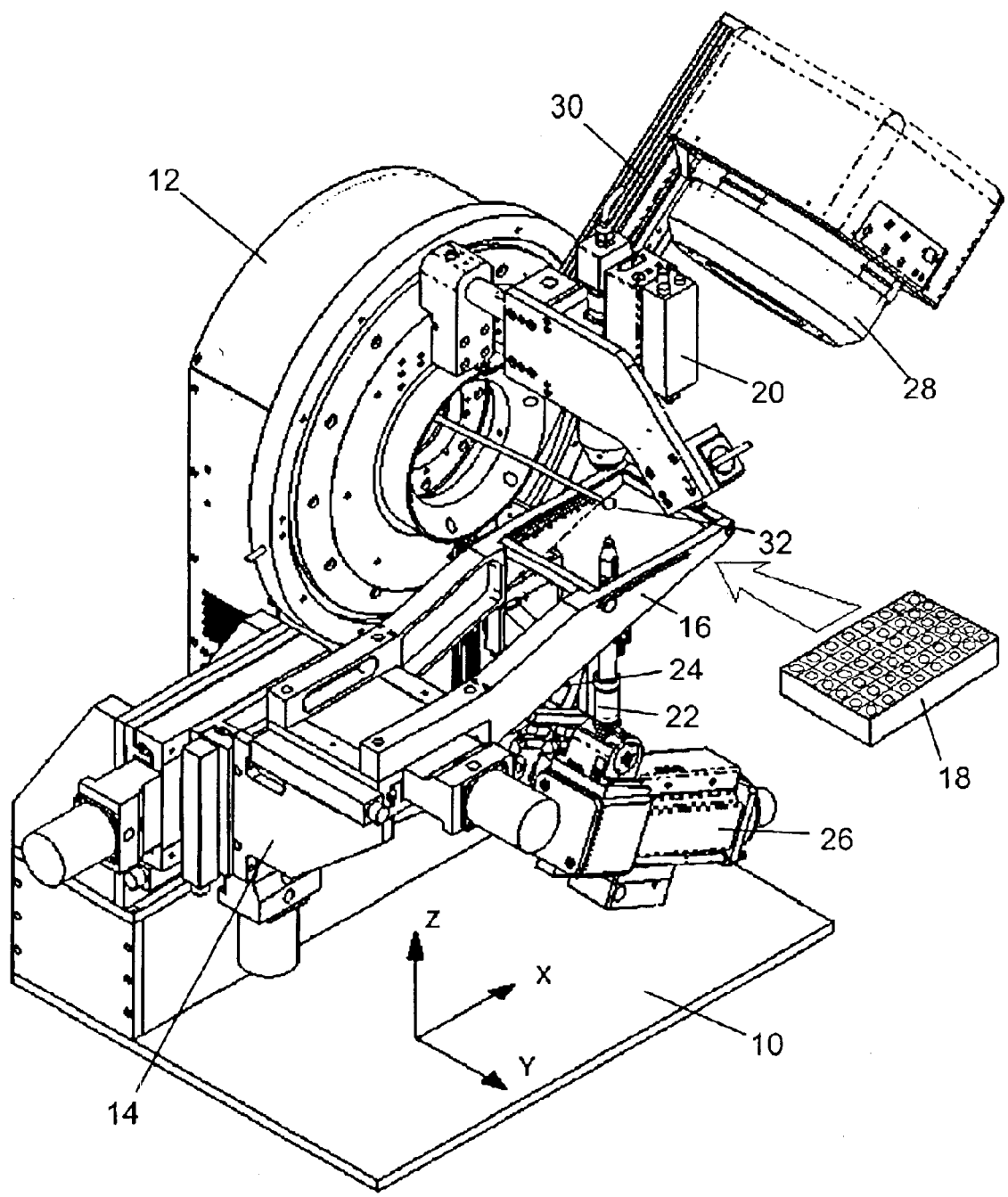
FIG. 1 is a perspective view of a transmission mode x-ray diffraction analysis system according to the present invention.

Shown in perspective in FIG. 1 is a transmission mode x-ray diffraction analysis apparatus for use in combinatorial chemistry applications. A base 10 of the apparatus supports a vertical two-circle goniometer 12. The base also supports a translation stage 14 that may be adjusted in three dimensions (i.e., the "X," "Y" and "Z" directions shown in the figure). The translation stage 14 is offset relative to the location at which a sample is positioned for analysis. Connected to the translation stage 14 is a transmission sample stage 16 that extends the "instrument center," which is the position in the apparatus at which a sample under test is located. In the vicinity of the instrument center, the sample stage 16 has a sample plate holder upon which a sample plate 18 may be mounted. The sample plate holder supports the plate along its outside edge, such that the portion of the sample plate in which the samples are located is exposed from both above and below.

With a sample tray in place, positioning adjustments may be made using laser/video alignment system 20, which is attached to the outer circle of the goniometer 12. Such devices are known in the art, e.g., as described in U.S. Pat. No. 5,359,640, which is incorporated herein by reference. Such systems use a laser focused on the instrument center in combination with a video camera apparatus to detect the position of a sample under test. Using this position data, the translation stage may be adjusted either manually or automatically to precisely position the sample for testing purposes.

In the system of FIG. 1, positioned below the sample support 16 is x-ray optics assembly 22, which includes an x-ray source that directs x-ray energy to the sample under test through the base of the sample tray 18. The optics assembly includes x-ray tube/shield 26, and is mounted to a stationary dovetail track 24 that is connected to the slot rim of the goniometer 12. Two-dimensional x-ray detector 28 is mounted to dovetail track 30 which, in turn, is connected to the inner circle of the goniometer 12. The detector is positioned at a diffraction angle appropriate for detecting the x-ray energy diffracted from the sample under test. Also shown in the figure is retractable beamstop 32, which prevents the direct x-ray beam from optics assembly 22 from reaching the detector. It is positioned above the instrument center, and may be retracted during sample loading and positioning.

Figure 2:
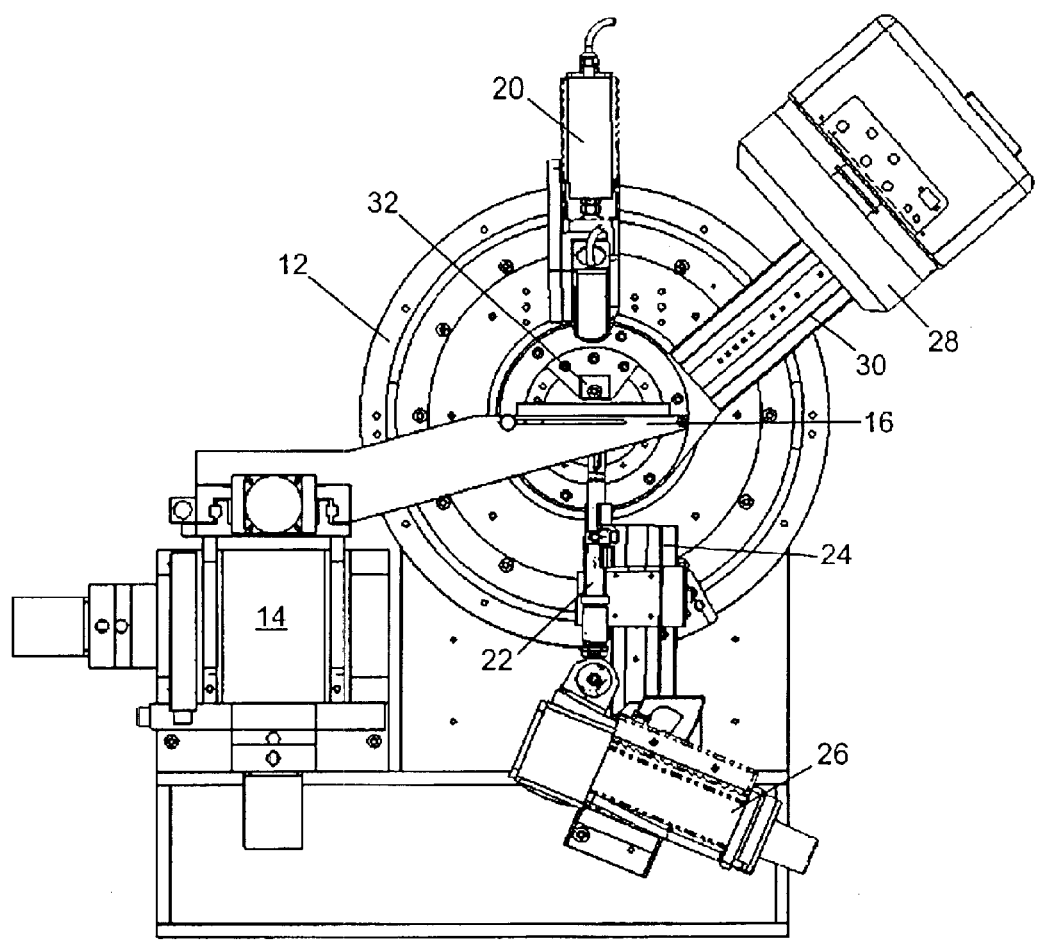
FIG. 2 is a front view of the system of FIG. 1.

A front view of the system is shown in FIG. 2. In this figure, the relative angular positioning of the different apparatus components may be more clearly seen. The goniometer 12 has two different coaxial rotation segments, one associated with the inner circle and one associated with the outer circle. As shown, the dovetail track 30 (and, correspondingly the x-ray detector 28) is connected to the inner circle of the goniometer 12, while the x-ray optics apparatus 26 is connected to the slot rim of the goniometer. Relative angular positioning between the x-ray source and the detector provides the ability to perform diffraction measurements at various Bragg angles from 0° to 90°.

As is also apparent from FIG. 2, the offset-mounted translation stage 14 keeps the bulk of the sample positioning mechanism out of the way of the x-ray source, allowing the direction of x-ray energy from underneath the sample tray. The translation stage may be motorized, allowing the automated positioning of the sample using the data collected with the laser/video alignment system 20. X-Y translation of the translation stage is used to bring each cell of the sample tray to the instrument center, while a Z-translation provides a precise sample height alignment based on the input from the laser/video system 20.

As can be seen from the figures, the orientation of the translation stage 14 and sample support 16 allow a sample tray to be maintained in a horizontal plane. This enables the testing of liquid or loose powder samples without spillage. It is desirable to make the opening of the sample support 16 adjustable to allow it to support sample trays of different sizes and shapes. Nevertheless, it provides a rigid support for the sample trays held therein.

The two-dimensional detector 28 is preferably a high-sensitivity and low-noise detector. This allows the testing of samples for which the yield is very low, e.g., in the range of grams or milligrams. By rotation of the inner circle of the goniometer, the relative detection angle of the detector 28 may be changed. This may be used to change the diffraction angle for different sample trays or different samples of the same tray, or the same sample or samples may be tested at different diffraction angles. A counterbalancing weight may be used if the detection apparatus is particularly heavy or positioned at a large sample-to-detector distance. The position of the laser/video apparatus 20 is dependent upon the position of the outer circle of the goniometer, to which it is attached. It may be moved to the alignment position, or away to provide more space for the detector. The video portion of the apparatus may include a motorized video zoom that allows control of the magnification and the field of view.

As mentioned above, the system also may include a retractable beamstop 32. Preferably, the beamstop is also motorized, allowing it to be extended and retracted as part of an automated testing routine. In its extended position, the beamstop blocks the direct x-ray beam, and prevents its reaching the detector 28 during low-angle measurements. In between the testing of different samples, the beamstop is retracted to facilitate sample loading and to prevent obstruction of the laser/video system 20 during sample alignment. A modified beamstop may also be used, such as that described in U.S. Pat. No. 6,163,592, which is incorporated herein by reference. This patent describes a beamstop that allows measurement of the x-ray beam energy and the diffracted x-rays simultaneously, and the disclosure of that patent is incorporated herein by reference.

It is preferable that the testing routine be automated such that each of the samples in the sample tray is tested in sequence. A software routine controls the testing procedure and implements all the necessary steps for performing the diffraction analysis. This includes automatically locating each sample cell and moving the samples sequentially to the instrument center. The position of each sample is precisely aligned and the beamstop is extended into place. The x-ray source is then activated and the diffraction signal is detected and processed. The process is repeated for each of the samples of the sample tray.

In the illustrated embodiment, the system may be operated in either a "beam up" or a "beam down" configuration. In the arrangement shown in FIG. 2, the x-ray source 26 is below the sample tray, so that the beam passes upward first through a portion of the sample tray, thereafter encountering the sample material itself. However, by rotating the two circles of the goniometer 12, the system may be changed to the configuration shown in FIG. 3, in which the optics assembly 26 is located above the sample tray, and the detector 28 is located below. In this configuration, the sample support is at the same orientation, but the x-ray beam encounters the sample before the sample tray, and the diffracted x-rays must then pass through a surface of the sample tray to reach the detector 28.

Figure 4:
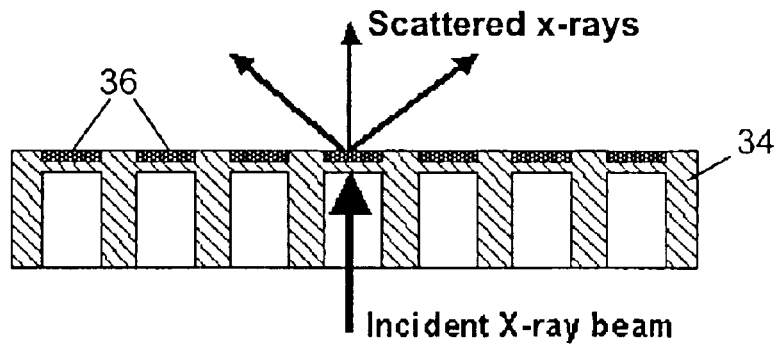
FIG. 4 is a cross-sectional front view of a sample tray for use with the system of FIG. 1 in a "beam-up" configuration.
Figure 5:
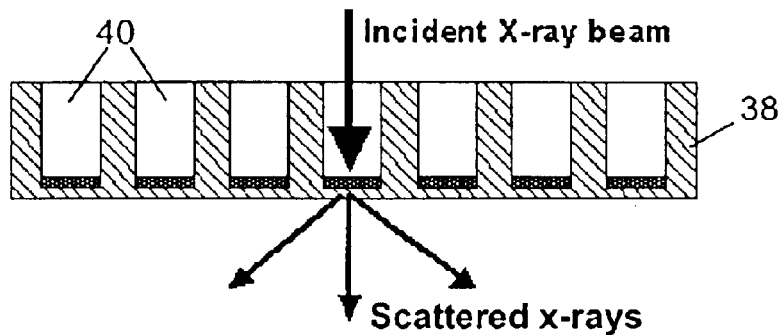
FIG. 5 is a cross-sectional front view of a sample tray for use with the system of FIG. 1 in a "beam-down" configuration.

The beam-up and the beam-down configurations, respectively, may be desirable in different situations. The sample trays may also differ in their structure to better accommodate the particular configuration of the system. When loaded with samples for combinatorial chemistry applications, these sample trays are sometimes referred to as "material libraries." Shown in FIG. 4 is a sample tray 34 for use with a beam-up type system. As shown, the sample materials are located in small sample wells 36 atop the tray 34. The incident x-ray beam passes through a cavity of the tray under the sample under test, through a bottom surface of the well containing the sample under test and to the sample material. A sample tray 38 that is better suited for a beam-down configuration is shown in FIG. 5. In this tray, the sample wells 40 are much deeper, so that the majority of the empty space is above the sample rather than below it. The incident x-ray beam passes downward through the hollow space in the sample well above the sample under test, and encounters the sample at the base of the well. The diffracted x-ray energy then passes outward through the bottom surface of the sample tray 38.

Figure 3:
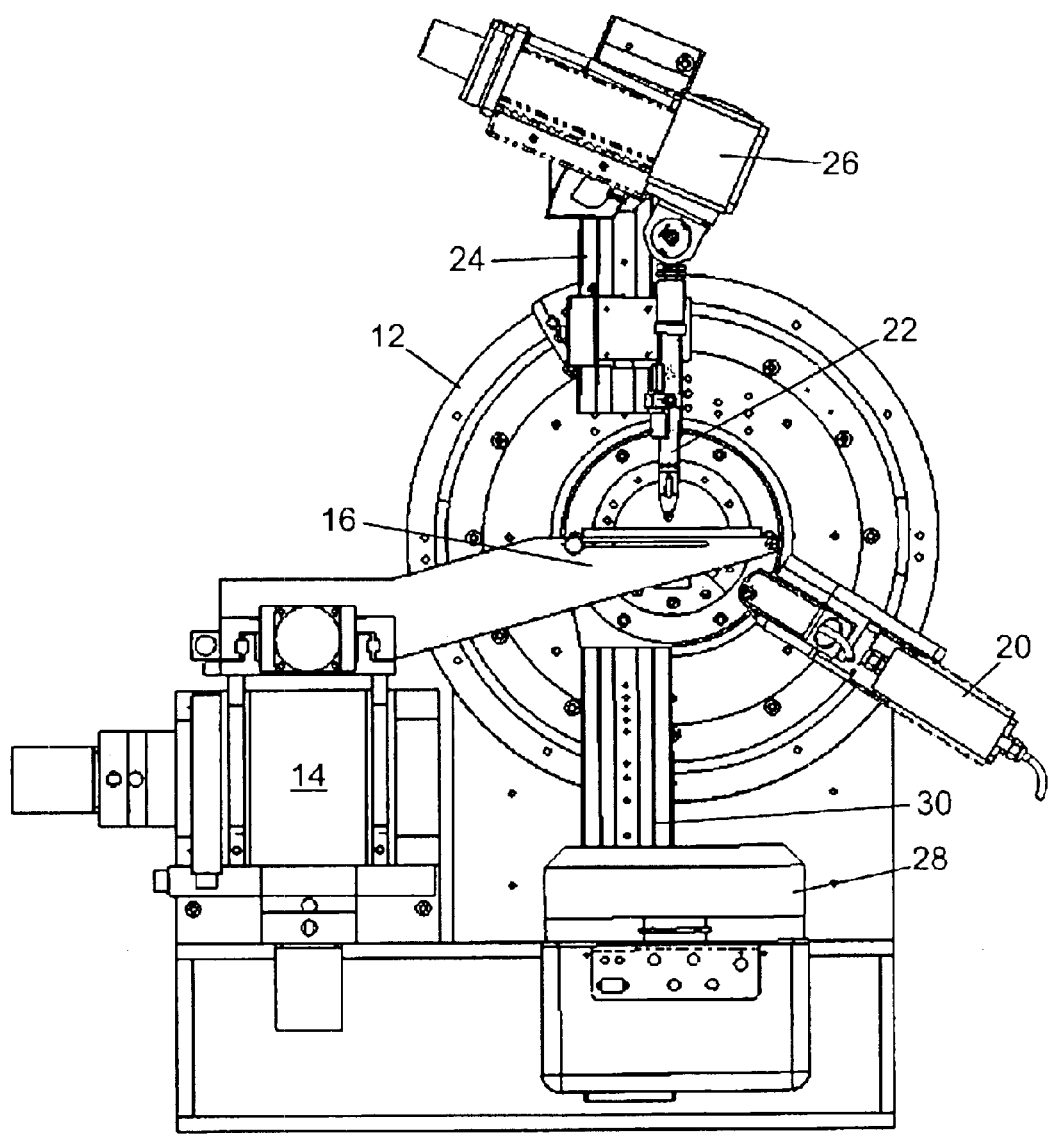
FIG. 3 is a front view of the system of FIG. 1 in a "beam-down" configuration.
Figure 6:
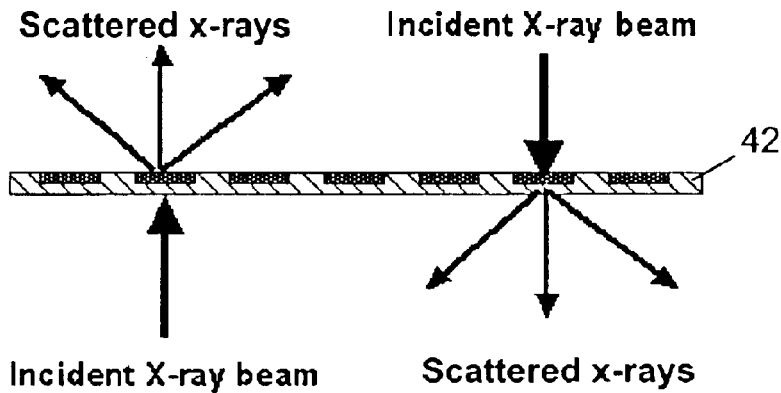
FIG. 6 is a cross-sectional front view of a sample tray for use with the system of FIG. 1 in either a "beam-up" or a "beam-down" configuration.

Each of the sample trays of FIGS. 3 and 4 is better suited for one of the beam-up or beam-down configurations. However, it is possible to have a tray that may be equally appropriate for either configuration. Shown in FIG. 6 is a sample tray 42 having a narrow profile. Indeed, the thickness of the sample tray is only enough to accommodate the thin sample layers and a thin sample tray surface to support them from below. With this thin profile, the sample tray is well suited for either beam-up or beam-down operation.

What is claimed is:

1. An x-ray diffraction screening apparatus for performing x-ray diffraction testing on a plurality of samples in a sample tray, the apparatus comprising:
    a sample support on which the sample tray is mounted;
    an x-ray source located to a first side of the sample support;
    an x-ray detector located to a second side of the sample support opposite the first side; and
    a translation stage that is rigidly connected to the sample support, and that is movable in at least two mutually perpendicular directions, the translation stage being offset from a position of the sample tray during testing, and the sample support having an extending portion by which it is connected to the translation stage.

2. An apparatus according to claim 1 wherein the x-ray source and detector are each mounted on a goniometer, the goniometer having an axis about which mounting circles of the goniometer are rotatable.

3. An apparatus according to claim 2 wherein the translation stage is offset in a radial direction relative to the goniometer axis further than an outermost circle of the goniometer.

4. An apparatus according to claim 2 where the x-ray source and detector are mounted on the same circle of the goniometer.

5. An apparatus according to claim 1 further comprising a video camera that provides an image of a sample on the sample support to be tested.

6. An apparatus according to claim 5 wherein the positioning of the sample as shown in the image is used to adjust the position of the translation stage.

7. An apparatus according to claim 5 further comprising a laser used to illuminate the position of the sample to be tested.

8. An apparatus according to claim 1 wherein the x-ray source is located below the sample support.

9. An apparatus according to claim 1 wherein the x-ray source is located above the sample support.

10. An apparatus according to claim 1 wherein the apparatus is changeable between an arrangement in which the x-ray source is below the sample support to an arrangement in which the x-ray source is above the sample support.

11. An apparatus according to claim 1 further comprising a beamstop located between the sample support and the detector, the beamstop at least partially blocking a portion of an x-ray beam from the x-ray source that passes through the sample.

12. An apparatus according to claim 11 wherein the beamstop is movable away from the position in which it blocks said portion of the x-ray beam.

13. An apparatus according to claim 12 wherein the movable beamstop is motorized.

14. An apparatus according to claim 1 wherein the apparatus is automated, such that samples in the sample tray are each tested sequentially, with the translation stage being moved to change which sample is in position for testing.

15. An apparatus according to claim 14 wherein the automatic operation of the system follows a testing software routine.

16. An apparatus according to claim 14 further comprising a video apparatus that provides an image of a sample on the sample support to be tested, the video image being used during movement of the translation stage to allow precise positioning of the sample.

17. An apparatus according to claim 16 further comprising a laser that illuminates a sample to be tested, the laser illumination being detected in the video image and used during movement of the translation stage.

18. An apparatus according to claim 1 wherein the translation stage is movable in three mutually perpendicular directions.

19. An apparatus according to claim 1 wherein the sample support supports the sample tray along the edges, such that it does not obstruct portions of the sample tray below the samples.

20. An apparatus according to claim 1 wherein the sample support is maintained in a horizontal orientation.

21. A transmission mode x-ray diffraction screening apparatus for performing x-ray diffraction testing on a plurality of samples in a sample tray, the apparatus comprising:

a sample support on which the sample tray is mounted;

an x-ray source mounted to a goniometer and located to a first side of the sample support;

an x-ray detector mounted to the goniometer and located to a second side of the sample support opposite the first side;

a video imaging apparatus that produces image data of the location at which is positioned a sample to be tested; and a translation stage that is rigidly connected to the sample support, and that is movable in three mutually perpendicular directions, the translation stage being offset from a position of the sample tray during testing, and the sample support having an extending portion by which it is connected to the translation stage, wherein the translation stage is controlled automatically to move the sample support and change which sample is in position for testing, movement of the sample support being responsive to the image data from the video imaging apparatus.

22. A method of performing x-ray diffraction testing on a plurality of samples in a sample tray, the method comprising:

locating the sample tray on a sample support that is rigidly connected to a translation stage, and that is movable in at least two mutually perpendicular directions, the translation stage being offset from the sample support by an extending portion that connects the sample support and the translation stage;

directing x-rays toward a sample under test with an x-ray source located to a first side of the sample support; and detecting diffracted x-ray energy with an x-ray detector located to a second side of the sample support opposite the first side.

23. A method according to claim 22 wherein the x-ray source and detector are each mounted on a goniometer, the goniometer having an axis about which mounting circles of the goniometer are rotatable.

24. A method according to claim 23 wherein the translation stage is offset in a radial direction relative to the goniometer axis further than an outermost circle of the goniometer.

25. A method according to claim 22 further comprising imaging a sample location of the apparatus with a video camera.

26. A method according to claim 25 further comprising positioning the sample with the translation stage using image data from the video camera.

27. A method according to claim 25 further comprising illuminating the sample location with a laser.

28. A method according to claim 22 wherein the x-ray source is located below the sample support.

29. A method according to claim 22 wherein the x-ray source is located above the sample support.

30. A method according to claim 22 wherein the apparatus is changeable between an arrangement in which the x-ray source is below the sample support to an arrangement in which the x-ray source is above the sample support.

31. A method according to claim 22 further comprising at least partially blocking a portion of an x-ray beam from the x-ray source that passes through the sample with a beamstop located between the sample support and the detector.

32. A method according to claim 31 wherein the beamstop is movable away from the position in which it blocks said portion of the x-ray beam.

33. A method according to claim 22 wherein the apparatus is automated, such that samples in the sample tray are each tested sequentially, with the translation stage being moved to change which sample is in position for testing.

34. A method according to claim 33 wherein the automatic operation of the system follows a testing software routine.

35. A method according to claim 22 wherein the translation stage is movable in three mutually perpendicular directions.

36. A method according to claim 22 wherein the sample support supports the sample tray along the edges, such that it does not obstruct portions of the sample tray below the samples.

* * * * *